United States Patent [19]

Schoenwald et al.

[11] Patent Number: 5,776,482
[45] Date of Patent: Jul. 7, 1998

[54] TETRAHYDROQUINOLINE ANALOGUES FOR USE IN GLAUCOMA TREATMENT

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 625,721

[22] Filed: Mar. 29, 1996

[51] Int. Cl.$^6$ .............. A61F 2/00; C07D 215/00; C07D 215/36; C07D 215/16
[52] U.S. Cl. .............. 424/427; 424/428; 546/152; 546/153; 546/134; 546/164
[58] Field of Search .............. 424/427, 428; 514/210, 307, 311, 314, 312, 233.5, 212, 278, 654, 649, 913, 655; 546/108, 18, 156, 157, 158, 153, 152, 134, 164

[56] References Cited

U.S. PATENT DOCUMENTS

| | | | |
|---|---|---|---|
| 4,260,764 | 4/1981 | Johnson | 546/153 |
| 4,273,775 | 6/1981 | Sarges | 424/256 |
| 4,309,432 | 1/1982 | Tanaka et al. | 424/258 |
| 4,309,545 | 1/1982 | Johnson | 546/108 |
| 4,322,425 | 3/1982 | Yabuuchi et al. | 424/258 |
| 4,340,737 | 7/1982 | Johnson | 546/108 |
| 4,555,513 | 11/1985 | Hamada et al. | 514/311 |
| 4,678,793 | 7/1987 | Klaus et al. | 514/311 |
| 4,738,851 | 4/1988 | Schoenwald et al. | 424/488 |
| 4,798,830 | 1/1989 | Lasslo et al. | 514/314 |
| 4,801,593 | 1/1989 | Hodson et al. | 514/307 |
| 4,808,619 | 2/1989 | Evans et al. | 514/278 |
| 4,843,082 | 6/1989 | Biller et al. | 514/311 |
| 4,855,291 | 8/1989 | Davies | 514/312 |
| 4,952,573 | 8/1990 | LeClerc et al. | 514/311 |
| 5,219,851 | 6/1993 | Hamilton et al. | 514/233.5 |
| 5,281,600 | 1/1994 | Kojima et al. | 514/311 |
| 5,322,859 | 6/1994 | Schoenwald et al. | 514/649 |
| 5,371,226 | 12/1994 | Mederski et al. | 546/156 |
| 5,382,576 | 1/1995 | Schoenwald et al. | 514/210 |
| 5,384,318 | 1/1995 | Eggler et al. | 514/212 |
| 5,416,095 | 5/1995 | Hanson et al. | 514/311 |
| 5,461,063 | 10/1995 | Kelleher et al. | 514/312 |

FOREIGN PATENT DOCUMENTS 1579230 of 0000 United Kingdom .

OTHER PUBLICATIONS

J.V. Braun, Chem. Ber. v. 42, pp. 2219–2227 (1909).
Prunte et al. "Topical SDZ GLC–756, A Novel Dopamine D–1 Antagonist and D–2 Agonist, Lowers Intraocular Pressure in Conscious Rabbits". Jpn. J. Ophthalmol., vol. 40, pp. 167–173, 1996.

Primary Examiner—Marian C. Knode
Assistant Examiner—Datquan Lee
Attorney, Agent, or Firm—Zarley, McKee, Thomte, Voorhees, & Sease

[57] ABSTRACT

Tetrahydroquinoline analogues and compositions containing them for topically treating glaucoma to effectively reduce intraocular eye pressure.

9 Claims, No Drawings

TETRAHYDROQUINOLINE ANALOGUES FOR USE IN GLAUCOMA TREATMENT

BACKGROUND OF THE INVENTION

Glaucoma, which some estimate affects 2 million adults over 40, is an impairment of vision caused by too much fluid pressure within the eye.

Surgical treatment for glaucoma is effective; however, it is expensive, and some surgeons will use surgery only as a last resort.

Glaucoma stems from an excess of fluid behind the cornea, the three-layered tissue that acts as a window to let light enter. Fluid-carrying nutrients, such as potassium and glucose, constantly wash the inside of the cornea to keep it healthy, much as tears wash the outside of the cornea.

In some middle-aged adults fluids build up faster than can be absorbed back into the blood for one of two reasons: the ciliary body (a tiny tissue behind the iris) may excrete too much fluid, or the fluid may not drain off at the normal rate.

Either way, the excess fluid damages the optic nerve. At first, a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral (through the mouth)—each have a peculiar set of side effects.

To make the long journey, oral drugs must be dosed in very high concentration. One class of drugs, called carbonic anhydrase inhibitors, slow the formulation of fluid by inhibiting a chemical reaction at the ciliary body. Along with their well-tested effectiveness comes nausea, tingling in fingers and toes, and other side effects. Oral drugs generally do not, however, cause side effects in the eye, but the systemic delivery system is slow and causes other side effects.

From the above discussion, it can be seen that there is a continuing need for the development of new drugs that can be applied topically in order to avoid systemic effects, and which may at the same time still be highly effective. This, of course, necessitates that the compound be one which will, first of all, effectively evoke a response which will provide the correct intraocular pressure, and secondly, penetrate the cornea rapidly and distribute well to the active site, i.e. ciliary body of the eye, or perhaps the trabecular meshwork. It goes without saying that compounds which are active as intraocular pressure inhibitors, but have limited penetrability across the cornea and to the site of activity are, as a practical matter, of limited value in developing truly effective topical glaucoma treatments, even though they may have some test activity in vitro, i.e. in a test tube. Put another way, if the compound does not have the correct distribution and penetration properties, its chances of being pharmacologically active, when topically applied to an affected eye in patients, are small at best. Thus, it is important if one is developing effective topical medicaments that they be active in vitro, and that they be active when actually applied to an affected eye from the standpoint of penetrating the cornea and reaching the active site for effective treatment of glaucoma.

Our own previous U.S. Pat. No 5,382,576, issued Jan. 17, 1995, entitled 1-AZA-1-ARYLCYCLOALKANES AS TOPICAL GLAUCOMA TREATMENT AGENTS demonstrated that very simple derivatives of 1-phenylpiperidine have the ability to significantly lower intraocular pressure by approximately 25–30% in white rabbits, presumably by a serotonin-based mechanism. That patent reported a previously unrecognized pharmacophore.

There is a continuing need for the development of new pharmacophores that will function as active topicals in order to continue the effort to develop important new antiglaucoma agents. In accordance with this invention, the applicants have developed certain 1,2,3,4-tetrahydroquinolines as serotonin antagonists for use in glaucoma treatment. These compounds, such as 1-ethyl-1,2,3,4-tetrahydroquinoline, have been reported as new compounds many years ago, J. V. Braun, "Uber das Festigkeitsverhaltnis des Piperidin- und des Tetrahydrochinolin-Ringes," Chem.Ber.v.42, p.2219–2227, (1909).

While these compounds per se are known, such as 1-ethyl-1,2,3,4-tetrahydroquinoline, no disclosure of a utility for these compounds is disclosed in the literature, nor is there any recognition of the fact that they may function as serotonin receptors, and therefore be topically active as glaucoma treatment agents.

Accordingly, it is a primary object of the present invention to provide a new series of compounds that are serotonin antagonists, but are unassociated structurally with those made in the past.

Another objective is to develop compounds that are topically effective glaucoma treatments with enhanced corneal penetration, ciliary body distribution properties, and which are compounds of quite simplistic chemical structure from the standpoint of their pharmacophore. This latter fact is important in finding the minimum structure necessary to exert a particular pharmacological action, in this case lowering of (intraocular pressure) IOP.

It is yet another objective of the present invention to prepare new compounds and new treatment methods using those compounds for glaucoma that can be used topically to avoid the undesirable side effects of most systemic treatments.

An even further objective of the present invention is to prepare and use new compounds, differing in structure from those normally regarded as likely candidates for topical actives, which obviously therefore have a new pharmacophore, and therefore open new areas for potential screening for other topically effective candidates.

An even further object of the invention is to prepare a pharmaceutical composition using these compounds or their biologically active salt forms as effective topical treatment for glaucoma.

The method and manner of accomplishing each of the above objectives, as well as others, will become apparent from the detailed description of the invention which follows hereinafter.

SUMMARY OF THE INVENTION 1,2,3,4-tetrahydroquinolines, particularly 1-ethyl-1,2,3,4-tetrahydroquinolines, are used as effective topical glaucoma treatment agents. These compounds represent a simple structure and a new pharmacophore for topical glaucoma treatment.

DETAILED DESCRIPTION OF THE INVENTION

It is not presently known what the precise mechanism of action of the 1,2,3,4-tetrahydroquinolines is in effectively treating glaucoma. It is only known that these compounds are topically active. It is believed that they are not carbonic anhydrase inhibitors, and that they could work by some other treatment mechanism. Work is currently underway to provide further information on receptor site binding mechanisms, which should reveal the true mechanism of operation. Applicant, however, is not bound by any theory of operation of the present invention, and instead relies upon the simple fact that the compounds do work topically. It is, however, known from the standpoint of investigating several members of the above-identified class that the pharmacophore, i.e. the minimum structure necessary to exert the defined intraocular lowering pharmacological effect, seems to be 1,2,3,4-tetrahydroquinoline. These compounds have the following formula:

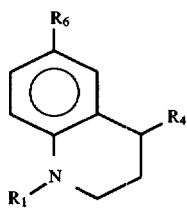

In the above general formula $R_1$ represents a simple alkyl, preferably $C_1$ to $C_8$ alkyl, and $R_4$ and $R_6$ may be the same or different and represent hydroxy, hydroxy alkyl, preferably $C_1$ to $C_6$ hydroxy alkyl, or fluoro. The most preferred compound is 1-ethyl-1,2,3,4-tetrahydroquinoline, where $R_1$ is ethyl, $R_6$ is hydrogen, and $R_4$ is also hydrogen.

The 1,2,3,4-tetrahydroquinolines which can be used to provide effective topical drugs of the present invention have a high degree of penetrability of the cornea so that they can have maximum effective delivery to the active site needed for glaucoma treatment.

Since all of these compounds are substituted amines, i.e. nitrogen, with all three positions filled, they will form hydrochloride salt forms which are known to be active. It is understood that the compounds referred to herein cover the compounds themselves as well as their biologically active salts.

Typically, the method of administration is simply preparing a water soluble salt (e.g. hydrochloride) with a suitable pharmaceutical carrier and topically administering the solution. The amount of active use in the composition should be from about 0.25% by weight to about 5% by weight for an eye drop composition, preferably from about 0.5% by weight to about 2.0% by weight. The important point is not the dose amount, but simply that it be an amount that is effective in treating glaucoma, and yet not be so strong as to provide eye irritation or side effects. Generally, amounts within the ranges herein specified are satisfactory.

The diluent for the eye drop composition may be an isotonic eye treatment carrier buffered to a pH of from about 4 to about 8, and typically it will contain small amounts of conventional wetting agents and anti-bacterial agents. The preferred pH is within the range from about 6.8 to about 7.8 and contain sufficient sodium chloride or equivalent to be isotonic. Anti-bacterial agents, where they are included, for example benzalkonium chloride, may be within the range of from about 0.004% (W/V) to about 0.02% (W/V) of the composition.

In conjunction with the evaluation of the present invention and its unexpected results, it is important to distinguish between topical application for treating glaucoma and oral dosing for treating glaucoma. This has been mentioned previously, but it is emphasized here again that topical application (dropped into the eye) has the significant advantage of avoiding most of the systemic side effects, but for effectiveness it is essential that the compound or compounds be actively transported into the eye at sufficient levels to reach the proper receptor site. Thus, topically active compounds must have the correct distribution and penetration properties. The 1,2,3,4-tetrahydroquinolines, as herein discussed and as demonstrated by the data below, are topically active and have highly effective pharmacological properties as well.

The following examples are offered to further illustrate but not limit the compounds of the invention, the performance of the compounds of the invention, or the pharmaceutical compositions of the invention.

EXAMPLES

The following examples of certain compounds of the present invention obtained in accordance with conventional synthesis procedures earlier described, and in some instances obtained commercially, were tested for their topical effect in lowering IOP. IOP was measured using a pneumatonograph (Digilabs Model 30D, Cambridge, Mass.) and 1–2 drops of 0.5% proparacaine hydrochloride used topically for anesthesia. IOP is measured in both eyes. The active drug (2%) is dissolved in a pH 7.4 phosphate buffer and instilled (50 µL) into the lower conjunctival sac of the right eye only.

The "IOP recovery rate assay", as reported by Vareilles and Lotti (Ophthal. Res., 13, 72–79, 1981.), was used. In this assay 20% sodium chloride solution was infused into the marginal ear vein of New Zealand White rabbits for 10 minutes at a rate of 1 mL/min (N=12). IOP was measured at 15, 25, 35, 45, 60, 75, 90 and 120 minutes with an applanation pneumatonometer (Digilab Model D). Fifty µL of a 2% solution or suspension of the derivative containing a pH 7.4 phosphate buffer was administered topically to the right eye 60 minutes before the start of the sodium chloride infusion. Control animals were given vehicle without drug.

The hypertonic sodium chloride solution causes a temporary decline in IOP, which returns to normal IOP in about 90 minutes if no drug is administered. IOP gradually returns to normal at a constant rate, but more slowly if the in vivo secretion rate of aqueous humor is reduced due to the presence of drug. The return to normal IOP is measured from the positive linear slope, which is a measure of the constant rate of return to normal IOP and begins at about 30–45 minutes after starting the NaCl infusion. A comparison of the slope with and without the addition of test agent to the rabbit eye is expressed as "% decrease in slope".

In the above procedure the compound 1-ethyl-1,2,3,4-tetrahydroquinoline lowered IOP by 30% in New Zealand White rabbits, using the IOP recovery rate assay above described.

The following compounds, when used in this similar assay, are also demonstrated to show equal effectiveness with the preferred 1-ethyl-1,2,3,4-tetrahydroquinoline:

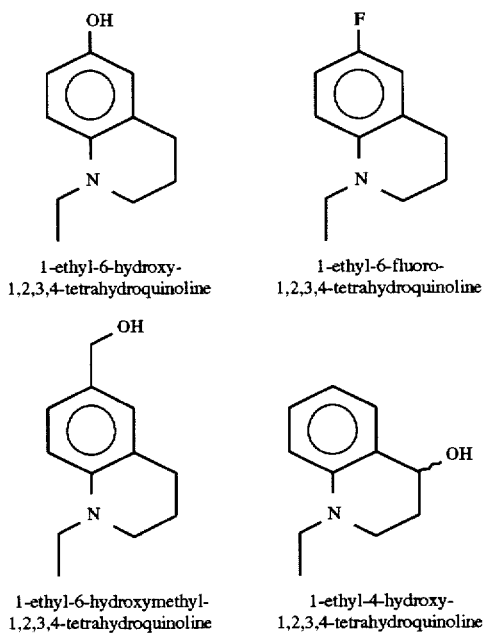

1-ethyl-6-hydroxy-1,2,3,4-tetrahydroquinoline 1-ethyl-6-fluoro-1,2,3,4-tetrahydroquinoline 1-ethyl-6-hydroxymethyl-1,2,3,4-tetrahydroquinoline 1-ethyl-4-hydroxy-1,2,3,4-tetrahydroquinoline The following claims are intended to define the invention with the understanding that certain changes may be made in the structures therein described and still come within the spirit and scope of the invention. For these changes, Applicant relies upon proper application of the Doctrine of Equivalents to provide the coverage equitably and legally allowed for the invention.

What is claimed is:

1. A method of reducing intraocular eye pressure, said method comprising:

topically applying to an affected eye a therapeutically effective intraocular eye pressure reducing amount of a 1,2,3,4-tetrahydroquinoline compound of the following formula:

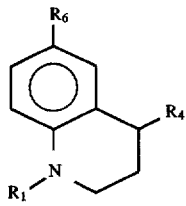

wherein $R_1$ is ethyl, $R_4$ is hydrogen or hydroxy, and $R_6$ is hydrogen, hydroxy or fluoro or a hydroxy $C_1$ to $C_6$ alkyl.

2. The method of claim 1 wherein the compound is administered from an eye drop composition containing from about 0.25% by weight to about 5% by weight of the compound in the eye drop composition.

3. The method of claim 1 wherein the compound is administered in a dose of from about 0.5% by weight to about 2% by weight.

4. An ophthalmic composition comprising:

a therapeutically effective intraocular eye pressure reducing amount of a 1,2,3,4-tetrahydroquinoline compound in a pharmaceutically acceptable carrier, said compound having the following formula:

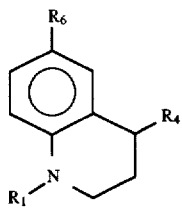

wherein $R_1$ is ethyl, $R_4$ is hydrogen or hydroxy, and $R_6$ is hydrogen, hydroxy or fluoro or a hydroxy $C_1$ to $C_6$ alkyl.

5. The composition of claim 1 wherein the compound is in a concentration of from about 0.25% by weight to about 5% by weight in the composition.

6. The composition of claim 1 wherein the compound is in a concentration of from about 0.5% by weight to about 2% by weight of said composition.

7. A method of reducing intraocular eye pressure, said method comprising:

topically applying to an affected eye a therapeutically effective intraocular eye pressure reducing amount of a 1-ethyl-1,2,3,4-tetrahydroquinoline.

8. The method according to claim 7 wherein the 1-ethyl-1,2,3,4-tetrahydroquinoline is selected from the group consisting of 1-ethyl-6-hydroxy-1,2,3,4-tetrahydroquinoline; 1-ethyl-6-fluoro-1,2,3,4-tetrahydroquinoline; 1-ethyl-6-hydroxymethyl-1,2,3,4-tetrahydroquinoline; and 1-ethyl-4-hydroxy-1,2,3,4-tetrahydroquinoline.

9. A method of reducing intraocular eye pressure, said method comprising:

topically applying to an affected eye the composition according to claim 4 comprising from about 0.25% to about 5% by weight of a 1,2,3,4-tetrahydroquinoline.

* * * * *